(12) United States Patent
Czeizler et al.

(10) Patent No.: US 11,931,598 B2
(45) Date of Patent: Mar. 19, 2024

(54) METHOD AND APPARATUS THAT INCLUDES GENERATING A CLINICAL TARGET VOLUME FOR THERAPEUTIC RADIATION

(71) Applicant: Varian Medical Systems International AG, Steinhausen (CH)

(72) Inventors: Elena Czeizler, Helsinki (FI); Esa Kuusela, Espoo (FI); Mikko Hakala, Helsinki (FI); Shahab Basiri, Helsinki (FI)

(73) Assignee: Varian Medical Systems International AG, Steinhausen (CH)

( * ) Notice: Subject to any disclaimer, the term of this patent is extended or adjusted under 35 U.S.C. 154(b) by 449 days.

(21) Appl. No.: 17/212,324

(22) Filed: Mar. 25, 2021

(65) Prior Publication Data

US 2022/0305285 A1 Sep. 29, 2022

(51) Int. Cl.
*G06T 7/11* (2017.01)
*A61N 5/10* (2006.01)

(52) U.S. Cl.
CPC ............. *A61N 5/103* (2013.01); *G06T 7/11* (2017.01); *G06T 2207/20081* (2013.01); *G06T 2207/20084* (2013.01); *G06T 2207/30096* (2013.01)

(58) Field of Classification Search
CPC . A61N 5/103; G06T 7/11; G06T 2207/20081; G06T 2207/20084; G06T 2207/30096
See application file for complete search history.

(56) References Cited

U.S. PATENT DOCUMENTS

| | | | |
|---|---|---|---|
| 10,898,726 B2* | 1/2021 | Ritter | A61N 5/1064 |
| 11,077,320 B1* | 8/2021 | Hibbard | G16H 20/40 |
| 2021/0012878 A1* | 1/2021 | Wu | G16H 70/20 |
| 2021/0052918 A1 | 2/2021 | Jin | |
| 2021/0298707 A1* | 9/2021 | Rosselet | A61B 6/032 |
| 2021/0361974 A1* | 11/2021 | Lachaine | G16H 40/63 |

OTHER PUBLICATIONS

International Search Report and Written Opinion from related International Application No. PCT/EP2022/057275 dated Jul. 13, 2022; 11 pages.

(Continued)

*Primary Examiner* — David P Porta
*Assistant Examiner* — Fani Polyzos Boosalis
(74) *Attorney, Agent, or Firm* — Fitch, Even, Tabin & Flannery LLP

(57) ABSTRACT

Image information regarding a particular patient is provided, which image information includes, at least in part, a tumor to be irradiated. These teachings can also include providing non-image clinical information that corresponds to the particular patient. A control circuit accesses the foregoing image information and non-image clinical information and automatically generates a clinical target volume that is larger than the tumor as a function of both the image information and the non-image clinical information. The control circuit can then generate a corresponding radiation treatment plan based upon that clinical target volume, which plan can be utilized to irradiate the clinical target volume.

14 Claims, 3 Drawing Sheets

(56) References Cited

OTHER PUBLICATIONS

Pouymayou, Bertrand et al., A Bayesian network model of lymphatic tumorprogression for personalized elective CTV definition in head and neck cancers; Physics in Medicine & Biology, (Aug. 14, 2019), vol. 64, No. 16, p. 165003, XP055937023.
Unkelbach, J. et al., SP-0272: The role of tumor growth models for CTV definition; Radiotherapy and Oncology, (Nov. 1, 2020), vol. 152, pp. S135-S136, doi:10.1016/S0167-8140 (21) 00296-6, ISSN 0167-8140, Ireland, XP055937082.
Meng, Xue et al., Noninvasive Evaluation of Microscopic Tumor Extensions Using Standardized Uptake Value and Metabolic Tumor Volume in Non-Small-Cell Lung Cancer, International Journal of Radiation: Oncology Biology Physics, (Feb. 1, 2012), vol. 82, No. 2, pp. 960-966, doi: 10.1016/J.IJROBP.2010.10.064, ISSN 0360-3016, XP028884123.

* cited by examiner

METHOD AND APPARATUS THAT INCLUDES GENERATING A CLINICAL TARGET VOLUME FOR THERAPEUTIC RADIATION

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

Delineating the so-called clinical target volume for a given patient is an important step in the radiation treatment planning process. Unfortunately, the clinical target volume often encompasses more than the gross tumor volume itself. Instead, and by way of example, subclinical regions beyond the gross tumor volume may be relevant considerations and regional lymph nodes may be included as well. In many cases one cannot achieve an appropriate clinical target volume by simply expanding the gross tumor volume by some uniform measure.

Generally speaking, delineating the clinical target volume for a given patient requires informed manual activity. The latter is both time-consuming and requires a high level of expertise. Furthermore, such an approach leads to great variability as between individuals and as between treatment centers.

BRIEF DESCRIPTION OF THE DRAWINGS

The above needs are at least partially met through provision of the method and apparatus that includes generating a clinical target volume for therapeutic radiation described in the following detailed description, particularly when studied in conjunction with the drawings, wherein.

Figure 1:
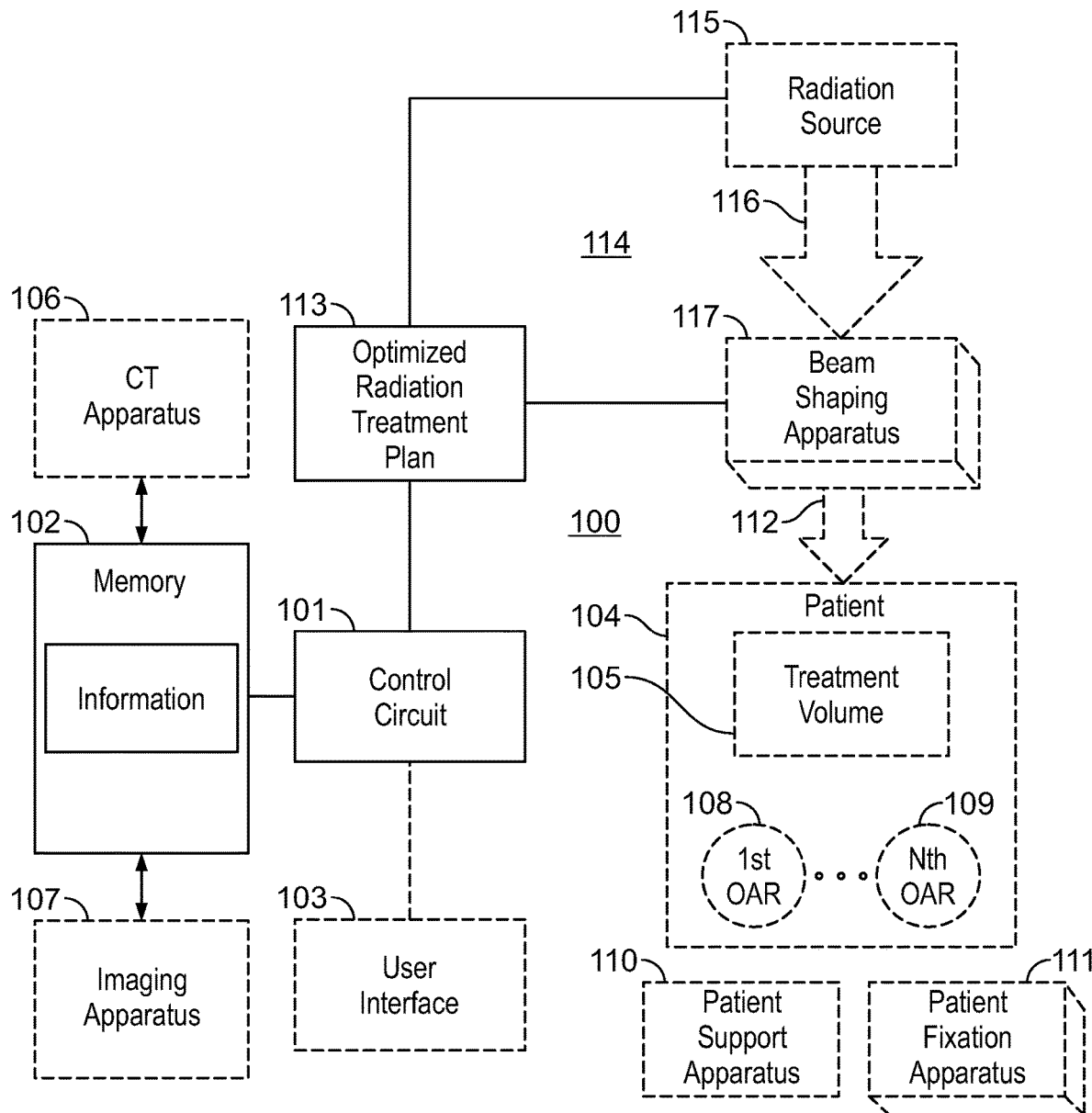
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate optimizing a patient treatment plan to administer therapeutic energy to a particular patient using a particular radiation treatment platform.

By one approach, these teachings provide for providing image information regarding the particular patient, which image information includes, at least in part, a tumor to be irradiated. These teachings can also include providing non-image clinical information that corresponds to the particular patient. A control circuit then accesses the foregoing image information and non-image clinical information and automatically generates a clinical target volume that is larger than the tumor as a function of both the image information and the non-image clinical information. The control circuit can then generate a corresponding radiation treatment plan based upon that clinical target volume, which plan can be utilized to irradiate the clinical target volume.

By one approach, the control circuit generates a gross tumor volume from the aforementioned image information. The control circuit can then automatically generate the clinical target volume that is larger than the tumor by automatically generating a clinical target volume that is larger than the tumor as a function of both the gross tumor volume and the non-image clinical information.

These teachings are highly practical in implementation and will accommodate, for example, a variety of different kinds of non-image clinical information. As one example, the non-image clinical information can comprise information regarding tumor type. As another example, the non-image clinical information can comprise information regarding tumor location in the particular patient. As yet another example, the non-image clinical information can comprise information regarding tumor grading. As yet another example, the non-image clinical information can comprise at least one (or both) of a logical component and at least one machine-learning model. By one approach, the foregoing machine-learning model can be configured to predict tumor laterality. By another approach, in lieu of the foregoing or in combination therewith, at least one such machine-learning model can be configured to comprise a segmentation model for at least one subclinical region.

By one approach these teachings separate clinical target volume segmentation into two general steps. First, a decision-making process selects regions to be included within the clinical target volume. Then, a convolutional neural network can automatically delineate the selected regions to yield the clinical target volume contour.

So configured, these teachings can support automatically generating clinical target volume contours for a given patient. By combining several different types of information, many nuances regarding a particular patient's presentation can be accommodated. Importantly, such an approach can effectively eliminate the variability that is inherent to a manual contouring process while also tending to yield better results on average than might otherwise be expected. These teachings can also provide usable and effective results in considerably less time than those skilled in the art might otherwise expect.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized radiation treatment plan 113 (such as, for example, an optimized radiation treatment plan). In this case the radiation treatment plan 113 is generated through an optimization process. A radiation treatment plan typically comprises specified values for each of a variety of treatment-platform parameters during each of a plurality of sequential fields. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

By one approach the control circuit 101 can operably couple to an energy-based treatment platform 114 that is configured to deliver therapeutic energy 112 to a corresponding patient 104 in accordance with the optimized energy-based treatment plan 113. These teachings are generally applicable for use with any of a wide variety of energy-based treatment platforms/apparatuses. In a typical application setting the energy-based treatment platform 114 will include an energy source 115 such as a source of ionizing radiation.

By one approach this energy source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the energy source 115 along that arcuate pathway, and may accordingly control when the energy source 115 starts moving, stops moving, accelerates, de-accelerates, and/or a velocity at which the energy source 115 travels along the arcuate pathway.

As one illustrative example, the energy source 115 can comprise, for example, a radio-frequency (RF) linear particle accelerator-based (linac-based) x-ray source, such as the Varian TrueBeam or Halcyon linear accelerator. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the energy source 115, and one or more energy-shaping apparatuses 117 (for example, beam-shaping apparatuses such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
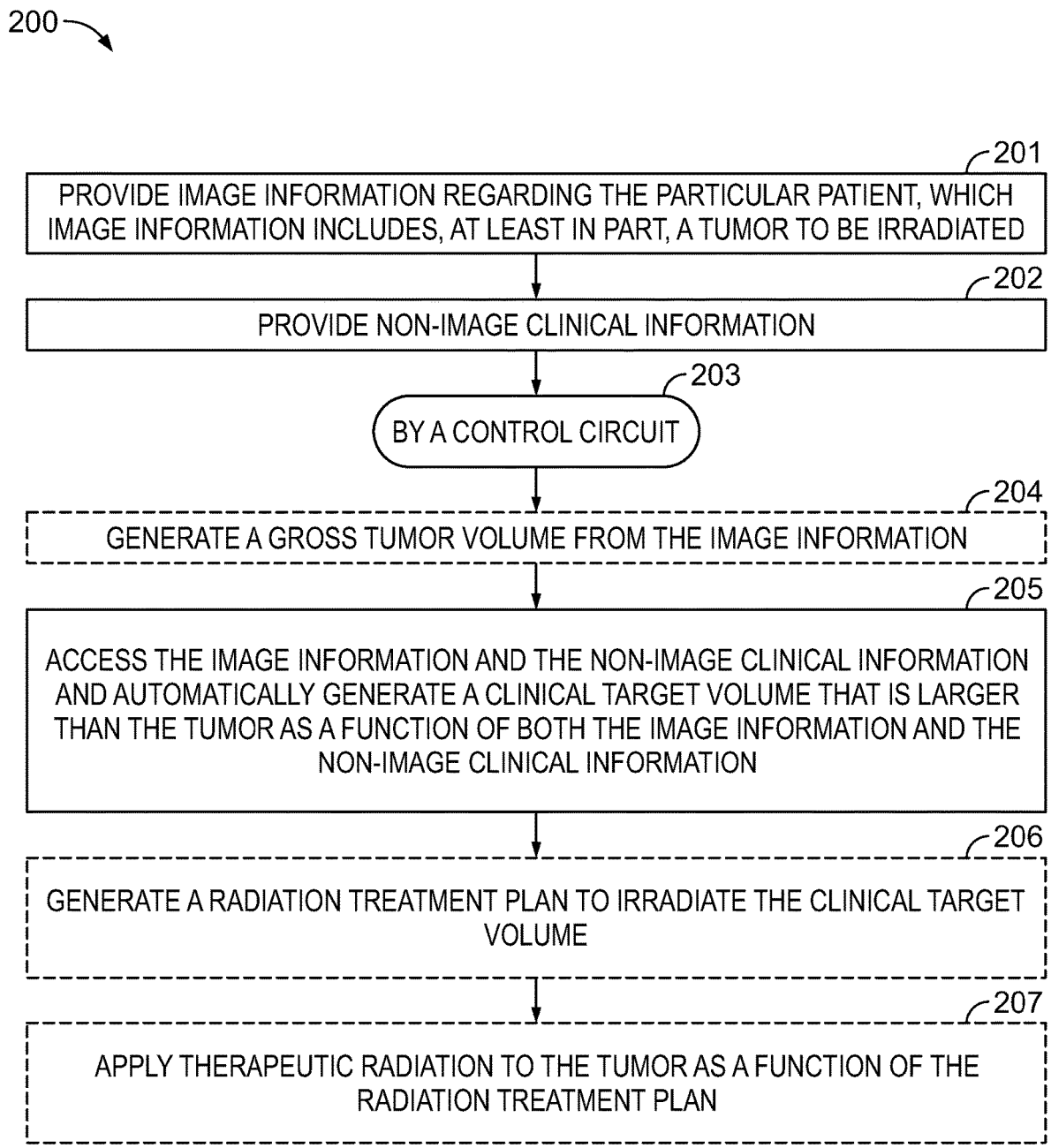
FIG. 2 comprises a flow diagram as configured in accordance with various embodiments of these teachings.

Referring now to FIG. 2, a process 200 that can be carried out, for example, in conjunction with the above-described application setting (and more particularly at least partially via the aforementioned control circuit 101) will be described.

Figure 3:
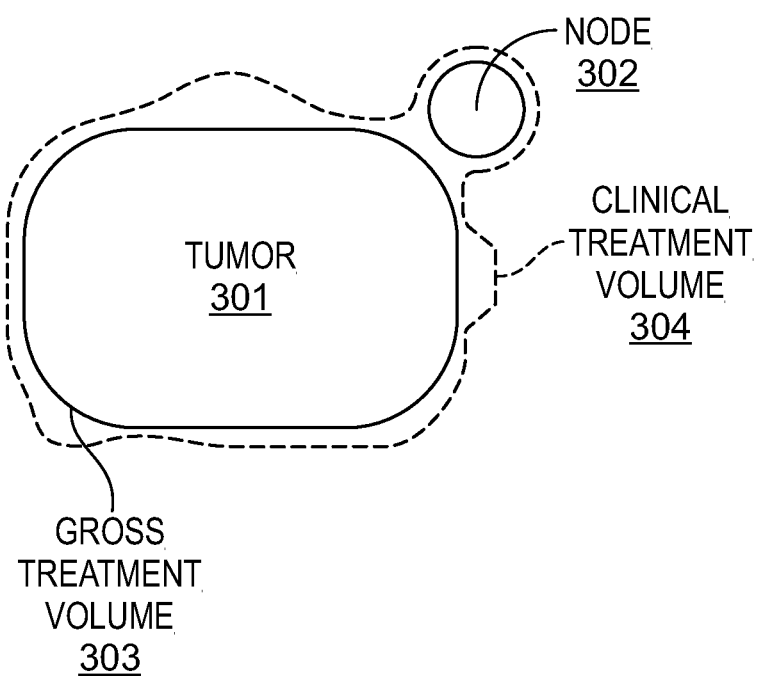
FIG. 3 comprises a schematic diagram as configured in accordance with various embodiments of these teachings.

At block 201, this process 200 provides image information regarding a particular patient 104. This image information includes, at least in part, a tumor to be irradiated. FIG. 3 provides an illustrative example in these regards where the tumor is denoted by reference 301. In many applications it will be beneficial if the image information also depicts any relevant organs at risk.

By one approach the control circuit 101 obtains this image information by accessing the aforementioned memory 102. These teachings will accommodate a variety of different kinds of image information including, by way of example, computed tomography (CT) images, magnetic resonance imaging (MRI) images, and/or positron emission tomography (PET) images. As another example, in lieu of the foregoing or in combination therewith, the image information may comprise gross tumor volume contours.

At block 202, this process 200 also provides non-image clinical information. These teachings are highly flexible in practice and will accommodate using one or more different kinds of non-image clinical information. As one example, the non-image clinical information can comprise information regarding tumor type. As another example, the non-image clinical information can comprise information regarding tumor location in the particular patient. As yet another example, the non-image clinical information can comprise information regarding tumor grading.

If desired, by one approach the non-image clinical information can comprise a logical component and/or one or more machine-learning models. The logical component can comprise a logical decision platform employing, for example, decision trees architecture or Markov logic networks (MLN) architecture. Employing an MLN approach may benefit many application settings. Because MLN's combine first-order logic with probabilistic graphical models, and MLN approach can readily incorporate protocol rules for selecting lymph node regions and other subclinical regions as first-order logic rules while also attaching a weight to each decision or formula. By integrating Markov logic model predictions in the first-order logic rules one can identify the set of regions that need to be put together to ultimately define the clinical target volume contours.

By one approach, the non-image clinical information can comprise a logical component (such as a Markov logic network) and at least two machine-learning models. By way of illustration and without intending to suggest any particular limitations with respect to these teachings, one such machine-learning model can comprise a model that predicts tumor laterality (that is, whether the tumor is sided or centralized with respect to patient geometry) and another such machine-learning model can comprise a segmentation model for at least one lymph node region or other subclinical regions. (Those skilled in the art will note that individual lymph nodes are typically relatively small and are not necessarily readily visible in CT images. It can therefore be convenient to define larger regions (that may contain several discrete "lymph nodes"). Also, it will be understood that as used herein, the expression lymph node region serves as a synonym for the expression "lymph node level.")

At this point in the process 200, at block 203 the control circuit 101 is employed (if such functionality has not already been utilized in the preceding steps).

At optional block 204, the control circuit 101 generates a gross tumor volume from the aforementioned image information. Those skilled in the art will understand that the gross tumor volume constitutes the grossly detectable tumor volume and hence represents the macroscopic extent of the tumor. The gross tumor volume therefore does not include any microscopic aspects thereof that extend outwardly from that macroscopically based periphery/margin. Contouring a gross tumor volume constitutes a known area of prior art endeavor and requires no further elaboration here.

Referring again to FIG. 3, the foregoing process yields a clinical treatment volume 304 that is larger than the tumor 301/gross treatment volume 303 to thereby accommodate microscopic aspects of the tumor 301 that extend beyond the foregoing and that also includes, for example, one or more lymph node regions 302 that are clinically appropriate to include within the region to be targeted to receive radiation. (When considering irradiation with prophylactic doses, typical irradiated volumes here can be volumes known as "lymph node levels." Lymph node levels are understood to contain the node (or possibly nodes) itself and part or all of a surrounding region. These elective lymph node levels are typically volumes that skilled, experienced persons expect to have microscopic tumor cells (occult metastases)).

While the clinical treatment volume 304 may include some uniform extended margin around the periphery of the tumor 301/gross treatment volume 303, these teachings 200 need not necessarily rely only upon such an approach. By taking non-image clinical information into account, the expanded margin of the clinical treatment volume 304 can be irregular as compared to the periphery of the tumor 301/gross treatment volume 303 in order to accommodate that non-image clinical information.

At block 205, the control circuit 101 accesses the aforementioned image information and the non-image clinical information and automatically generates a corresponding clinical target volume as a function of both the image information and the non-image clinical information. (When the control circuit has generated a gross tumor volume from the image information, the foregoing activity can include automatically generating the clinical target volume that is larger than the tumor 301 as a function of both the gross tumor volume and the non-image clinical information.)

At optional block 206, the control circuit 101 can generate an optimized radiation treatment plan 113 to irradiate the clinical target volume. And at optional block 207, this process 200 will accommodate applying therapeutic radiation 112 to the tumor as a function of that optimized radiation treatment plan 113.

A detailed example of a process flow that accords with these teachings will now be provided. It will be understood that the specific details in this example are intended to serve an illustrative purpose and are not intended to suggest any particular limitations with respect to these teachings.

To begin, this process flow can begin with a gross tumor volume auto segmentation model. This delineation can be accomplished as a function of the aforementioned image information regarding the particular patient. In this example the image information comprises medical imaging provided by a selected imaging modality (or modalities) such as CT imaging, PET imaging, or MRI imaging or a combination of two or more of these imaging modalities. This delineation yields the basic contours of the gross tumor volume. (By one approach, the so-contoured gross tumor volume comprises the so-called primary gross tumor volume (GTVp). If desired, this activity can also include contouring the gross tumor volume specific to one or more notable areas of interest (GTVn) in combination with the primary gross tumor volume, a total gross tumor volume (GTVt).) By one approach the foregoing contours are generated by an automated segmentation model. Such contours can also be manually drawn by an expert if desired.

Next, this process flow can apply a tumor location classifier comprising, for example, a model that identifies the physical location of the tumor given the foregoing gross tumor volume contour(s) and patient images depicting other structures within the patient.

Next, this process flow can apply a tumor laterality classifier comprising, for example, a machine learning model that predicts tumor laterality to thereby determine, for example, whether the tumor is sided or centralized with respect to patient geometry given the foregoing gross tumor volume contour(s) and patient images depicting other structures within the patient.

Next in this illustrative example, this process flow receives nodal stage information. This nodal stage information can comprise, for example, information regarding the status of relevant lymph nodes as the infiltration of lymph nodes by tumor cells represents a high tumor recurrence risk factor. By one approach this can comprise information provided by the user. By another approach, in lieu of the foregoing or in combination therewith, a machine learning model can be trained to predict such lymph node status as a function of relevant patient images.

In this illustrative example, the foregoing steps in this process flow are accomplished by machine learning models (or, at least in some instances and as desired, as input provided by a user). Other steps in this process flow can make use of logical decision platforms that model relevant protocol rules (based upon, for example, expert knowledge) for a given user, clinic, or multiple clinics. As noted above, Decision Trees or Markov Logic Networks can be readily employed in these regards.

For example, as a next step in this illustrative example, this process flow can undertake nodal selection logic sentences. These logic sentences encode a particular clinic's or oncologist's protocol and reasoning about which additional anatomic regions of the patient are to be irradiated prophylactically, and are thus to be included in the elective clinical target volume. The logic sentences can contain attributes related, but not limited, to tumor location, type, grading, and extension to nearby regions. The logic sentences can also permissibly contain rules that are non-rigid or that contain uncertainties.

Next in this illustrative example, this process flow employs a selected logical decision platform to determine a deduction of included lymph node regions. The logical decision platform can comprise a decision protocol, patient properties, and possibly other model predictions, such as machine-learning models. So configured, the logical decision platform deduces the solution for the list of lymph node regions to be included as irradiated targets.

In this illustrative example, this process flow may again employ general protocol rules as described above to accomplish auto segmentation of lymph node regions. The system of lymph node regions is a classification scheme for different lymph node regions that are related to tumor progression pathways.

As a next step in this illustrative example, this process flow can utilize a machine learning approach as described above to collect together the various contouring solutions for the tumor, subclinical regions, lymph node regions, and so forth to thereby define an aggregated contour. This process flow can then apply post-processing steps if desired to, for example, add one or more margins to the aggregated contour in order to output the final clinical target volume. (In practice, one often has more than one clinical target volume (CTV). For example, one CTV may contain the GTVp+ GTVn while another CTV contains the elective lymph node levels, where the latter CTV receives a lesser dose than the former. Accordingly, it will be understood that these teachings will accommodate having the aggregation and post-processing activity yield more than one CTV structure (and where the different CTV structures have different corresponding dose levels.)

So configured, these teachings will support, for example, advantageously combining and leveraging both a logical rules-based approach with machine learning approaches to automate, at least in large part, generating clinical target volumes that are larger than a targeted tumor using both image information and non-image clinical information. Furthermore, those skilled in the art will appreciate that these teachings provide for more than merely automating this particular planning activity and greatly reducing corresponding time requirements. In addition, these teachings can help reduce variability in contouring clinical target volumes as between different users and clinics without unduly reducing treatment efficacy or increasing unwanted collateral harm. At the same time, these teachings can reduce immediate real-time requirements for input from highly skilled and knowledgeable users.

Those skilled in the art will recognize that a wide variety of modifications, alterations, and combinations can be made with respect to the above-described embodiments without departing from the scope of the invention. Accordingly, such modifications, alterations, and combinations are to be viewed as being within the ambit of the inventive concept.

What is claimed is:

1. A method to facilitate irradiating a particular patient with therapeutic radiation, the method comprising:
providing image information regarding the particular patient, which image information includes, at least in part, a tumor to be irradiated;
providing non-image clinical information;
by a control circuit:
accessing the image information and the non-image clinical information and automatically generating a clinical target volume that is larger than the tumor as a function of both the image information and the non-image clinical information, wherein the non-image clinical information comprises at least one of tumor type, tumor location, and tumor grading;
generating a radiation treatment plan to irradiate the clinical target volume.

2. The method of claim 1 further comprising:
by the control circuit:

generating a gross tumor volume from the image information;

and wherein automatically generating the clinical target volume that is larger than the tumor as a function of both the image information and the non-image clinical information comprises automatically generating the clinical target volume that is larger than the tumor as a function of both the gross tumor volume and the non-image clinical information.

3. The method of claim 1 wherein the non-image clinical information comprises at least one of a logical component and at least one machine-learning model.

4. The method of claim 3 wherein the non-image clinical information comprises both of the logical component and the at least one machine-learning model.

5. The method of claim 4 wherein the non-image clinical information comprises each of the logical component and at least two machine-learning models.

6. The method of claim 3 wherein the at least one machine-learning model predicts tumor laterality.

7. The method of claim 3 wherein the at least one machine-learning model comprises a segmentation model for at least one subclinical region.

8. An apparatus to facilitate irradiating a particular patient with therapeutic radiation, the apparatus comprising:
   a memory having stored therein:
   image information regarding the particular patient, which image information includes, at least in part, a tumor to be irradiated;
   non-image clinical information, wherein the non-image clinical information comprises at least one of tumor type, tumor location, and tumor grading;
   a control circuit operably coupled to the memory and configured to:
   access the image information and the non-image clinical information and automatically generate a clinical target volume that is larger than the tumor as a function of both the image information and the non-image clinical information;
   generate a radiation treatment plan to irradiate the clinical target volume.

9. The apparatus of claim 8 wherein the control circuit is further configured to:
   generate a gross tumor volume from the image information;
   and wherein the control circuit is configured to automatically generate the clinical target volume that is larger than the tumor as a function of both the image information and the non-image clinical information by automatically generating the clinical target volume that is larger than the tumor as a function of both the gross tumor volume and the non-image clinical information.

10. The apparatus of claim 8 wherein the non-image clinical information comprises at least one of a logical component and at least one machine-learning model.

11. The apparatus of claim 10 wherein the non-image clinical information comprises both of the logical component and the at least one machine-learning model.

12. The apparatus of claim 11 wherein the non-image clinical information comprises each of the logical component and at least two machine-learning models.

13. The apparatus of claim 10 wherein the at least one machine-learning model predicts tumor laterality.

14. The apparatus of claim 10 wherein the at least one machine-learning model comprises a segmentation model for at least one subclinical region.

* * * * *